United States Patent
Lim et al.

(10) Patent No.: US 7,879,590 B2
(45) Date of Patent: Feb. 1, 2011

(54) METHOD TO ENGINEER MAPK SIGNALING RESPONSES USING SYNTHETIC SCAFFOLD INTERACTIONS AND SCAFFOLD-MEDIATED FEEDBACK LOOPS

(75) Inventors: Wendell A. Lim, San Francisco, CA (US); Caleb J. Bashor, San Francisco, CA (US)

(73) Assignee: Regents of the University of California, Oakland, CA (US)

( * ) Notice: Subject to any disclaimer, the term of this patent is extended or adjusted under 35 U.S.C. 154(b) by 475 days.

(21) Appl. No.: 12/047,767

(22) Filed: Mar. 13, 2008

(65) Prior Publication Data

US 2009/0233364 A1    Sep. 17, 2009

(51) Int. Cl.
*C12N 1/20* (2006.01)
*C12P 21/06* (2006.01)
(52) U.S. Cl. .................................. 435/254.2; 435/69.1
(58) Field of Classification Search .............. 435/254.2, 435/69.1
See application file for complete search history.

(56) References Cited

PUBLICATIONS

Park et al., Science, 299, 1061-1064, 2003.*

* cited by examiner

*Primary Examiner*—Maryam Monshipouri
(74) *Attorney, Agent, or Firm*—Richard Aron Osman

(57) ABSTRACT

Synthetic scaffold interactions and scaffold-mediated feedback loops are used to engineer MAPK signaling responses in cells.

20 Claims, 4 Drawing Sheets

Synthetic recruitment of pathway effectors to the MAP kinase scaffold protein Ste5 can selectively decrease or increase signaling pathway output.

Dynamicaly regulated recruitment of pathway effectors to the Ste5 scaffold can be used to build synthetic positive and negative feedback loops.

Strength of synthetic negative feedback circuit can be precisely tuned by altering recruitment affinity and inducible expression level of negative effector (Msg5)

Recruitment-based toolkit can be used to engineer diverse pathway architectures and response behaviors.

METHOD TO ENGINEER MAPK SIGNALING RESPONSES USING SYNTHETIC SCAFFOLD INTERACTIONS AND SCAFFOLD-MEDIATED FEEDBACK LOOPS

This work was made with Government support under grants awarded by DARPA (N66001-04-1-8901). The Government has certain rights in this invention.

FIELD OF THE INVENTION

The field of the invention is engineering MAPK signaling responses using synthetic scaffold interactions and scaffold-mediated feedback loops.

BACKGROUND OF THE INVENTION

Mitogen activated protein (MAP) kinase pathways (a cascade of three successive protein kinases) are a common molecular signal transduction system used to mediate eukaryotic cell responses to their environment. MAP Kinase pathways are used by mammalian cells to mediate cell growth, differentiation, apoptosis, stress response and immune response. They are also used in plants for environmental sensing. In different cells, this core pathway is reprogrammed to yield a tailored response.

Our invention provides a method to systematically reprogram MAP kinase signaling responses. The invention allows one to engineer and modify MAP kinase signaling behavior such that it is optimized for new target behaviors. This method can be used, for example, to engineer into yeast modified control systems for regulating metabolic processes, such as in engineered biofuel production.

Our method uses engineered feedback loops to modify pathway response. Much of the diversity in natural MAP kinase response behaviors is due to the fact that individual examples have distinct feedback loops overlaid on the core linear kinase cascade. As in electronic circuits, these feedback loops profoundly alter behavior—specific feedback architectures can lead to distinct classes of responses. By building specific synthetic feedback loops, we show that we can systematically engineer MAP kinase pathway behavior in living cells.

Our method for building novel feedback loops relies on the fact that MAP kinase pathways are organized by scaffold proteins—proteins (or a complex) that bind to the pathway members and facilitate their communication with one another and prevent miscommunication with incorrect molecules. Thus the scaffold is a hub that organizes the wiring of the pathway. In our method, by conditionally recruiting new pathway modulators to the scaffold, we can build positive or negative feedback loops (FIG. 2a).

In an illustrative embodiment, the method comprises three general classes of parts: 1) pathway modulators, 2) recruitment interaction pair, and 3) pathway induced promoter. The general logic is that one constructs a gene that consists of a pathway modulator that is fused to one of the interaction pair partners, and places this under the control of a promoter that is only activated when the MAPK pathway is turned activated. One then fuses the other interaction pair partner domain to the scaffold protein. Thus when the pathway is activated, it will lead to expression of the modulator-interaction domain fusion protein, which will then be recruited to the scaffold. When recruited to the scaffold, the modulator can strongly exert its effect; if this was a positive modulator, it would generate a positive feedback loop; if it was a negative modulator, it would generate a negative feedback loop.

In proof of principle experiments, we have used a variety of modulators and interaction pairs to build such illustrative feedback loops in the yeast mating MAP kinase pathway, including the positive activator of MAPKKK, Ste50, the negative modulators Msg5 (MAPK phosphatase—from yeast), OspF (MAPK phosphothreonine lyase—from *Shigella*), and YopJ (MAPK acetylase—from *Yersinia*), and the PDZ-peptide and pairs leucine-zipper heterodimerization interaction pairs; of course, alternative modulators and interaction pairs maybe substituted.

As detailed further below, our scaffold-based engineering method can be practiced in numerous variations. For example, multiple feedback loops can be layered to achieve more complex behaviors. Also, decoy interaction domains can be introduced to compete with the recruitment of pathway modulators to the scaffold. Together, these simple variations allow for more generation of more complex behaviors.

We have used these methods to alter MAP kinase pathways to show several distinct and useful classes of cellular behavior, including threshold sensing (ultrasensitve response), adaptation to continued stimulation, pulse response, delayed response, and accelerated response. In several cases we have demonstrated that by varying parameters such as recruitment interaction affinity or promoter strength, we can systematically tune the precise response behavior.

Our methods can be applied to systematically tune the behavior of any cell containing a MAP kinase pathway that is organized by a scaffold protein, or other comparable protein assemblies. Using the basic design framework outlined herein, and by exploring a finite range of system parameters, the pathway response behavior can be tuned as desired. Our methods are also suitable for constructing small combinatorial variants.

The methods can be used in any cell that uses MAPK signaling for a process of interest. Often the endogenous MAPK pathway behavior in a cell, while in principle useful for a desired function, might have quantitative response behaviors that are incompatible with the target function. Our methods can be used to tune the behavior such that it is optimized. This method could be useful for a wide range of applications, including: a) engineering cell lines with specifically tuned MAP kinase response behaviors optimized for drug screening; b) engineering therapeutic immune cells that detect tunable levels of antigen and respond in a tunable manner; c) engineering stem cells that respond to stimuli with precisely tunable differentiation or apoptotic responses; d) engineering plant cells that can detect specific signals and respond in tunable way, for example, detection of pathogens or noxious chemicals, or for production or agricultural purposes that require input controlled induction; and e) engineering yeast cells to provided control systems for regulating metabolic processes, such as in engineered biofuel production. In short, our invention provides general methods for achieving tunable control over a protein signaling pathway, by using recruitment pairs to introduce novel regulatory feedback loops into MAPK signaling pathways.

SUMMARY OF THE INVENTION

The invention provides methods and compositions for making and using engineered scaffold interactions to reshape MAP kinase pathway signaling dynamics. The invention provides synthetic, feedback-regulated MAP kinase pathways and cells comprising such synthetic pathways.

In one embodiment, the invention provides in a cell, a synthetic, feedback-regulated MAP kinase pathway having a signaling input and output, comprising: (a) a MAP kinase signaling pathway complex fused to a first binding partner; and (b) a MAP kinase signaling pathway effector fused to a second binding partner, wherein: (i) the first and second binding partners bind to recruit the effector to the complex; (ii) the effector functionally modulates the complex to provide a modulated output; and (iii) the modulated output in turn modulates effector activity, providing a regulatory feedback loop to the pathway.

In particular embodiments, the effector is a positive effector providing an increased, modulated output, or a negative effector providing a decreased, modulated output.

In particular embodiments, the modulated output increases effector activity to create a positive feedback loop, or decreases effector activity to create a negative feedback loop.

In particular embodiments, (a) the effector is a negative effector providing a decreased modulated output, and the yeast cell constitutively expresses a decoy that competes with the complex for the negative effector, effectively creating a pulse generator signaling pathway;

(b) the effector is a positive effector providing an increased modulated output, and the yeast cell constitutively expresses the positive effector, and inducibly expresses a negative effector, effectively creating an accelerator signaling pathway;

(c) the effector is a negative effector providing a decreased modulated output, and the yeast cell constitutively expresses the negative effector, and inducibly expresses a high-affinity decoy that competes with the complex for the negative effector, effectively creating an delay signaling pathway; or (d) the effector is a negative effector providing a decreased modulated output, and the yeast cell constitutively expresses the negative effector, and inducibly expresses a positive effector, that competes with the complex for the negative effector, effectively creating an ultrasensitive switch signaling pathway.

The invention also provides methods of making and using the subject compositions, including methods of genetically-engineering a cell, comprising genetically-engineering the cell to express the subject synthetic, feedback-regulated MAP kinase pathways.

DETAILED DESCRIPTION OF PARTICULAR EMBODIMENTS OF THE INVENTION

Figure 1:
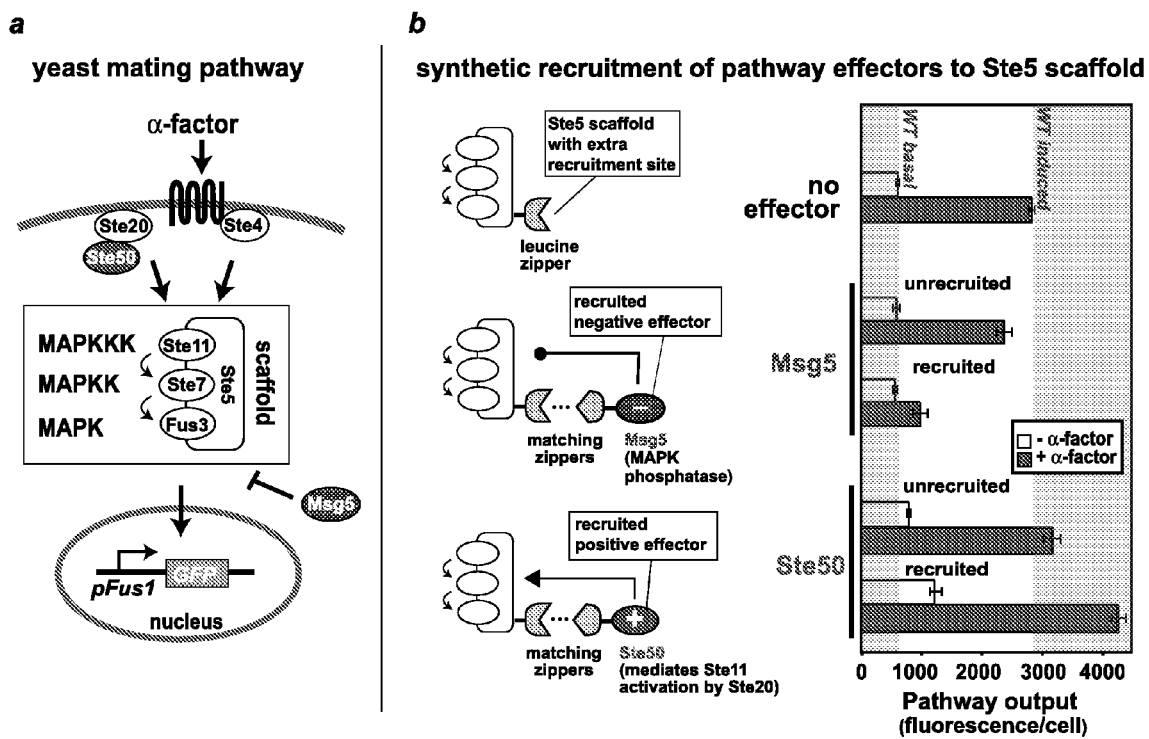
FIG. 1. Output from the yeast mating MAPK pathway can be significantly increased or decreased by artificially recruiting positive or negative pathway effectors: (a) Schematic of the mating MAPK pathway; (b) A heterodimeric leucine zipper protein-protein interaction pair is used to synthetically recruit new pathway effectors to the scaffold complex.

Scaffold proteins functionally link signaling molecules into specific linear pathways by physically assembling them into a complex. Scaffolds may also play a higher-order role as signal processing hubs: they can serve as the central target of regulatory feedback loops that precisely optimize signaling amplitude, timing, and duration. Here we demonstrate that scaffold proteins can be used as a platform to dramatically and systematically reshape output of the yeast mating MAP kinase pathway.

Synthetic positive and negative feedback loops were constructed by dynamically promoting or blocking the recruitment of pathway effectors to an artificial recruitment site fused to Ste5. These engineered circuits yielded a diverse range of systems behaviors: dose-response profiles could be systematically tuned, response time could be accelerated or delayed, and tunable adaptation could be added to the pathway. These findings illustrate how recruitment-based regulatory systems of scaffolded pathways are an extremely flexible platform for reprogramming complex cellular responses.

In living cells, many signaling proteins are physically organized into functional complexes. In a growing number of cases, these pathways are organized by scaffold proteins that contain binding sites for the individual proteins in the pathway [1, 2, 3]. Scaffolds promote efficient signaling between proper protein partners, and prevent improper crosstalk. Scaffold-mediated complexes are thus centralized hubs that direct information flow in a pathway.

While the primary function of a scaffold might be to specify the wiring of linear pathways, a scaffold can also serve as a central hub for feedback-based signal processing. Feedback loops that modulate the recruitment or function of pathway members on the scaffold can have significant effects on the quantitative behavior of the pathway, including on dose-response and pathway dynamics—the precise way in which output changes as a function of time. These quantitative input/output behaviors are critical for function, as the behavior of a pathway must often precisely match the requirements of the physiological context in which it operates [4]. Scaffolds may therefore provide a platform for evolutionarily tuning response behaviors for optimal fitness [5, 6].

We took a synthetic biology approach to explore this hypothesis: we asked whether a scaffold protein can be used as a platform for engineering synthetic feedback loops, and whether these loops can be used to systematically reshape pathway output behavior. We used the mating mitogen activated protein (MAP) kinase pathway as a model system. Several properties of this pathway make it a convenient model system for pathway engineering. First, connectivity of this pathway is coordinated by the scaffold protein Ste5, which binds the three core kinases—Ste11 (MAPKKK), Ste7 (MAPKK), and Fus3 (MAPK)—that successively phosphorylate and activate one another (FIG. 1a) [7, 8]. The critical role of the scaffold in determining pathway connectivity is highlighted by the observation that chimeric scaffolds can be used to redirect pathway input/output linkages [9, 10]. Second, MAP kinase pathways appear to have a relatively high degree of functional plasticity. MAPK cascades are found in all eukaryotic species, and in individual cases display widely varying systems behaviors. For example, the yeast mating pathway shows a largely linear transcriptional response [11, 12, 13], whereas the *Xenopus oocyte* maturation pathway displays an ultrasensitive, switch-like dose response [14]. MAPK pathways also show highly diverse dynamic behavior—some MAPK pathways yield a sustained response to stimulation, while others show a pulse-like transient response. These different pathway dynamics can determine the physiological output of the pathway [15-20].

Our goal was overlay the endogenous yeast mating pathway with synthetic feedback loops in order to systematically alter input/output behavior. We first tested whether constitutive recruitment of effector proteins could modulate pathway flux. We created a novel recruitment site on Ste5 by fusing a leucine zipper heterodimerzation module [21] to its C-terminus. Effector proteins fused to complementary zippers were then expressed and recruited to the scaffold (FIG. 1b). This leucine zipper pair interact in vitro with an affinity Kd=6 nM [21]. Two pathway effectors were recruited: Ste50 and Msg5 (FIG. 1a). Ste50 is a positive effector—it acts as an adaptor protein that promotes interaction of the MAPKKK Ste11 with its upstream activator, the PAK-like kinase, Ste20 [22, 23]. Msg5 is a negative effector—it is a MAPK phosphatase that can inactivate the phosphorylated form of the mating MAPK, Fus3 [24, 25]. When artificially recruited to the Ste5 scaffold via a leucine zipper interaction, Msg5 and Ste50 showed strong but opposite effects on pathway output, measured using a mating pathway-responsive GFP transcriptional reporter (GFP fluorescence detected by FACS). Recruitment of Ste50, the positive effector, increased the steady-state induced pathway output by nearly two-fold. Recruitment of Msg5, the negative effector, had the opposite effect—it essentially shut down the pathway, decreasing induced pathway output to near-basal (uninduced) levels. In contrast, neither unrecruited Ste50 nor unrecruited Msg5 had a significant effect on pathway output when expressed from the pCyc1 promoter. Thus the impact of both of these effectors on pathway flux is highly dependent on recruitment to the scaffold.

To build synthetic feedback loops using these novel recruited effectors, we placed effector expression under the control of a mating-dependent promoter (FIG. 1; FIG. 2a). Thus, the recruited effector would only be expressed after pathway activation. As shown in FIG. 2b, the engineered feedback loops lead to dramatic changes in pathway dynamics and dose response. The positive feedback loop, in which recruited Ste50 is expressed from a mating-dependent promoter, yields a significantly higher induced pathway output, as well as a more switch-like, or cooperative, dose-response. The apparent Hill coefficient (nH) increases from 1.06 in wild-type, to 2.31 in the engineered positive feedback circuit. A similar increase in pathway output has been demonstrated with positive feedback loops in which constitutive pathway alleles are expressed from a mating-responsive promoter [27].

The negative feedback loop, in which recruited Msg5 is expressed from a mating responsive promoter, displays adaptation—the cells respond initially like the wild-type circuit, but after 35 minutes, show a automatic decrease in pathway output, even with continued stimulation. Adaptation is a critical behavior for many biological sensing systems. It can be important to limit the duration of an output response to maintain homeostatic balance, or to prevent continued responses that are harmful or have a high metabolic cost. Adaptation is also critical for sensing systems like vision or bacterial chemotaxis that automatically desensitize to a continuous stimulus, allowing for detection changes in input level over a large dynamic range [28, 29].

One advantage of these engineered feedback loops is the ability to systematically explore how the alteration of specific circuit parameters affects pathway behavior. Simulation of the simple negative feedback circuit indicates that the degree of observed adaptation can be precisely tuned by adjusting feedback strength (FIG. 3a). We explored two experimental ways of adjusting feedback strength. For the first, we changed the strength of the leucine zipper recruitment interaction, since recruitment is essential for complete pathway repression by recruited Msg5 (FIG. 3b). We used a set of three leucine zipper pairs that bind with various affinities (Kd=6 nM, 40 nM, and 810 nM as measured in vitro; [21]). The second way to adjust feedback gain was to change the strength of the mating responsive promoter controlling expression of recruited Msg5 (FIG. 3c). We used a pair of mating promoters: pFig1, which has a strong transcriptional output, and pPrm2, which has a weak output. As predicted, increasing either the recruitment strength of the negative effector or the strength of its induced expression results in more rapid adaptation.

Because these synthetic feedback circuits rely on a recruitment-based mechanism, we reasoned that they could be modulated by competitive binding interactions that block recruitment of the effector protein to the scaffold. We tested whether competitive recruitment could be used to build a more complex negative feedback circuit that displayed a sharper, pulse-like activation response (FIG. 4a). We constitutively expressed a decoy leucine zipper that competes with the scaffold protein (Ste5-zipper) for binding to the negative effector (Msg5-zipper). Because the decoy has a higher affinity, it initially acts as a sink—after pathway activation, newly expressed negative effector is initially bound to the decoy zipper, thus preventing negative effector from binding to the scaffold. Only after binding of the effector to the decoy zipper becomes saturated is additionally expressed negative effector able to bind the scaffold and repress output. Indeed, this delayed negative feedback loop leads to the observed sharper pulse-like output. Moreover, the strength of the pulse can be modulated by adjusting the level at which the decoy zipper is expressed—higher decoy expression leads to a larger pulse and a longer delay until the adaptation phase begins.

The interplay of competing scaffold recruitment interactions and variable expression can be used to generate a number of diverse temporal behaviors, including systems with faster or slower response time. In any response circuit, the rise-time—how fast a response occurs after input—can be important for function. For example, a pathway that detects a highly toxic stress signal may require a very fast response. Other pathways may require a delayed response, if for example the response is energetically very costly or if the system in which the pathway operates has a high level of input noise (a delay circuit could filter against accidental mis-activation by transient input, while allowing activation by a sustained input).

We were able to alter the mating pathway to show a strongly accelerated response time, while still maintaining a maximal pathway output comparable to that observed in the wild-type (FIG. 4b). In this accelerator circuit, the positive effector (Ste50-zipper) is constitutively expressed, but the negative effector (Msg5-zipper, high affinity) is inducibly expressed. The positive effector leads to a rapid initial response. However, before a strongly amplified output level is reached, the negative feedback loop (induced expression of the high affinity negative effector) restores the system to an intermediate steady-state. This result supports the paradigm that negative autoregulation combined with increased amplitude can result in a response with an accelerated rise time [30].

We also generated a delay circuit by constitutively expressing a negative effector (Msg5zipper) and inducibly expressing a high affinity decoy zipper (FIG. 4c). The pathway initially shows extremely weak response to stimulation because the recruited negative effector keeps the pathway essentially shut off. After a delay time of ~50 minutes, however, a sufficient level of pathway activation is reached, and expression of the high affinity decoy zipper displaces the negative effector, allowing pathway activation.

Competition between positive and negative effectors for recruitment to the scaffold can also be used to dramatically alter dose-response behavior, in addition to pathway dynamics. We built an extremely cooperative, ultrasensitive switch by constitutively expressing a negative effector (Msg5-zipper) and inducibly expressing a positive effector (Ste50-zipper, high affinity) (FIG. 4d). This circuit is actually a double positive feedback loop—the stimulus-induced expression of Ste50-zipper has the direct effect of increasing pathway output, but also has the indirect effect of displacing the negative effector from the scaffold and relieving its inhibitory effect. The dose response profile for the resulting circuit shows a dramatic increased in cooperativity (apparent Hill coefficient nH=2.9 vs. 1.1 observed for no-feedback circuit).

We have used a simple principle—recruitment of pathway effectors to a scaffold—to systematically modify a single MAPK pathway so that it displays a wide range of input/output behaviors. Because the effect of these components on pathway flux occurs through the simple currency of protein-protein interaction, pathway behavior can be tuned by simply altering binding affinities, as well as by allowing competition between different, related interaction elements [31]. These results demonstrate that a protein scaffold can act as a flexible information processing hub—a highly programmable platform for tuning system input/output behavior.

DETAILED DESCRIPTION OF THE DRAWINGS

FIG. 1. Output from the yeast mating MAPK pathway can be significantly increased or decreased by artificially recruiting positive or negative pathway effectors to the scaffold protein Ste5. (a) Schematic of the mating MAPK pathway. Stimulation by alpha-factor activates the G-protein coupled receptor, Ste2, and heterotrimeric Gbeta subunit, Ste4. Activated Ste4 recruits the Ste5 scaffold complex to the membrane, allowing PAK-like kinase Ste20 (membrane-localized) to activate MAPKKK Ste11. Ste11 and its downstream kinases, Ste7 (MAPKK) and Fus3 (MAPK), are co-localized on the Ste5 scaffold protein. Activation of the MAPK cascade leads to the mating transcriptional program (pathway reporter: Fus1 promoter-GFP). In this work we have focused on pathway effectors that are not part of the core kinase cascade: Ste50 (positive effector, blue) promotes activation of Ste11 by Ste20 by interacting with both proteins; Msg5 (negative effector, red) is a MAPK phosphatase that dephosphorylates activated Fus3.

(b) A heterodimeric leucine zipper protein-protein interaction pair is used to synthetically recruit new pathway effectors to the Ste5 scaffold complex. A basic zipper module was fused to Ste5 and the complementary acidic zipper module was fused to either a negative effector, Msg5, or a positive effector, Ste50 (this recruited leucine zipper pair has a Kd=6.1 nM). As a negative control ("unrecruited"), Ste50 and Msg5 were fused to the non-complementary zipper. Effect of recruitment on pathway output was assessed by measuring pFus1-GFP expression by FACS. Basal output was measured prior to stimulation; induced output was measured 120 min. after stimulation with a saturating concentration of alpha-factor (2 µM). Errors represent std. dev. of three experiments. Unshaded area in the bar graph highlights the input-dependent output change observed for the wild-type pathway. All strains were constructed from a ΔSte5 background using an integrated Ste5-zipper fusion expressed from the native pSte5 promoter. Effector-zipper fusions were expressed from the pCyc1 promoter and integrated using either pRS305 (Msg5) or pRS304 (Ste50) plasmids. At these expression levels, Ste50 and Msg5 show significant effects on induced pathway output (Ste50 increase; Msg5—decrease), but only when recruited to Ste5, where a higher effective concentration may facilitate their actions on Ste11 and Fus3. Recruitment of these effectors has minimal effects on uninduced pathway output. Control experiments in which recruitment domain orientation was reversed (basic zipper fused to effectors and acidic zipper was fused to scaffold) gave qualitatively similar results.

Figure 2:
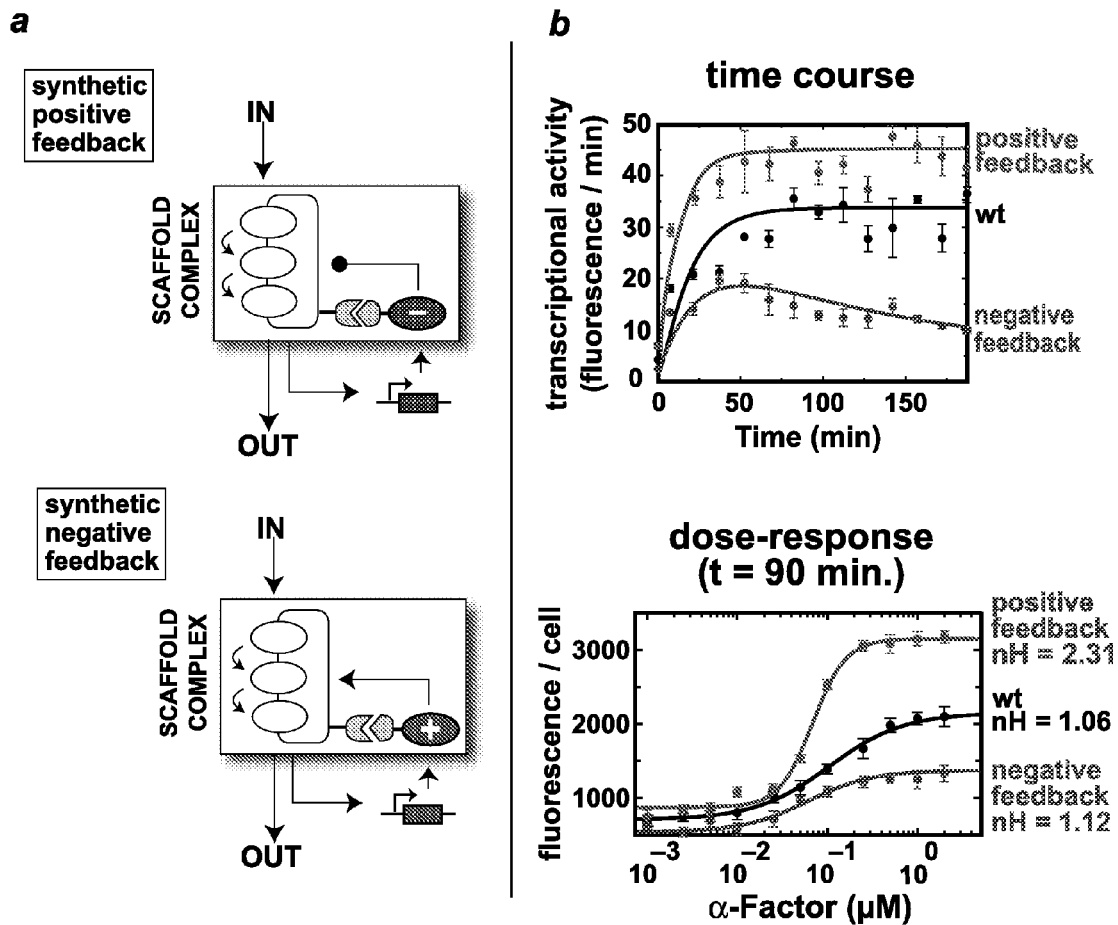
FIG. 2. Dynamically regulated recruitment of pathway effectors to the Ste5 scaffold can be used to build synthetic positive and negative feedback loops: (a) Schematic of negative and positive feedback loop design; (b) Experimental analysis of synthetic feedback loops.

FIG. 2. Dynamically regulated recruitment of pathway effectors to the Ste5 scaffold can be used to build synthetic positive and negative feedback loops. (a) Schematic of negative and positive feedback loop design. Effector-leucine zipper fusions (negative Msg5; positive—Ste50) are expressed from a mating-responsive promoter (pFig1). Stimulation of the pathway upon addition of pheromone leads to expression of the effector-zipper fusion, which is then recruited to the Ste5-scaffold where it can strongly exert its effect, either decreasing or increasing pathway flux.

(b) Experimental analysis of synthetic feedback loops. In order to facilitate FACS analysis, we implemented all feedback circuits in a Δfar1 background strain (designated as WT). This strain does not undergo mating induced cell cycle arrest, thus cells are more uniform in size for FACS analysis. The synthetic negative feedback circuit (red), upon stimulation with a saturating concentration of alpha-factor (2 µM), shows an initial rate of pathway activation similar to the wild-type (no synthetic feedback), but peaks at ~35 min and shows adaptation to a steady-state that is ~3-fold lower than the wild-type. The synthetic positive feedback circuit (blue) shows time course dynamics similar to the wild-type, but with steady-state output ~1.5 fold greater. The dose-response curves show that the positive feedback circuit displays significantly more switch-like activation, with an apparent Hill coefficient nH=2.31 compared to nH=1.06 for the wild-type.

Figure 3:
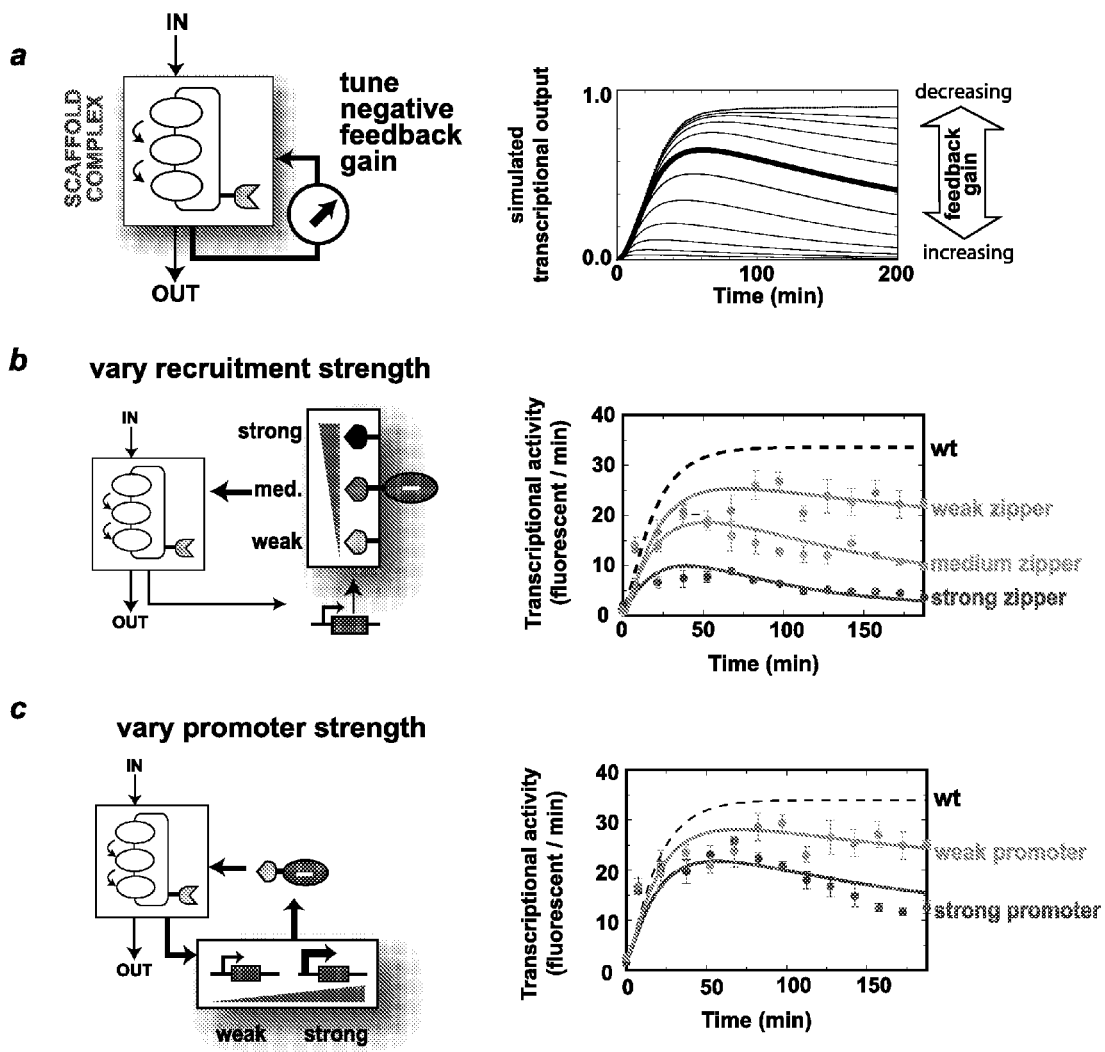
FIG. 3. Strength of synthetic negative feedback circuit can be tuned by either altering recruitment affinity or inducible expression level of negative effector: (a) Simple computational model of synthetic negative feedback loop predicts that adjustments in feedback gain should tune adaptation behavior; (b) Adjusting feedback gain by varying effector recruitment strength; (c) Adjusting feedback gain by varying effector promoter strength.

FIG. 3. Strength of synthetic negative feedback circuit can be tuned by either altering recruitment affinity or inducible expression level of negative effector. (a) Simple computational model of synthetic negative feedback loop predicts that adjustments in feedback gain should tune adaptation behavior.

(b) Adjusting feedback gain by varying effector recruitment strength. Three variants of the leucine zipper fused to Msg5-zipper were used which bind to the complementary, Ste5—fused zipper with different affinities (strong, Kd=6.1 nM; medium, Kd=41 nm; weak, Kd=810 nM).

(c) Adjusting feedback gain by varying effector promoter strength. The negative effector, Msg5-zipper, is dynamically expressed from a mating induced promoter. Two promoters of varying inducible strength were used: strong promoter, pFig1; and weak promoter, pPrm1.

Figure 4:
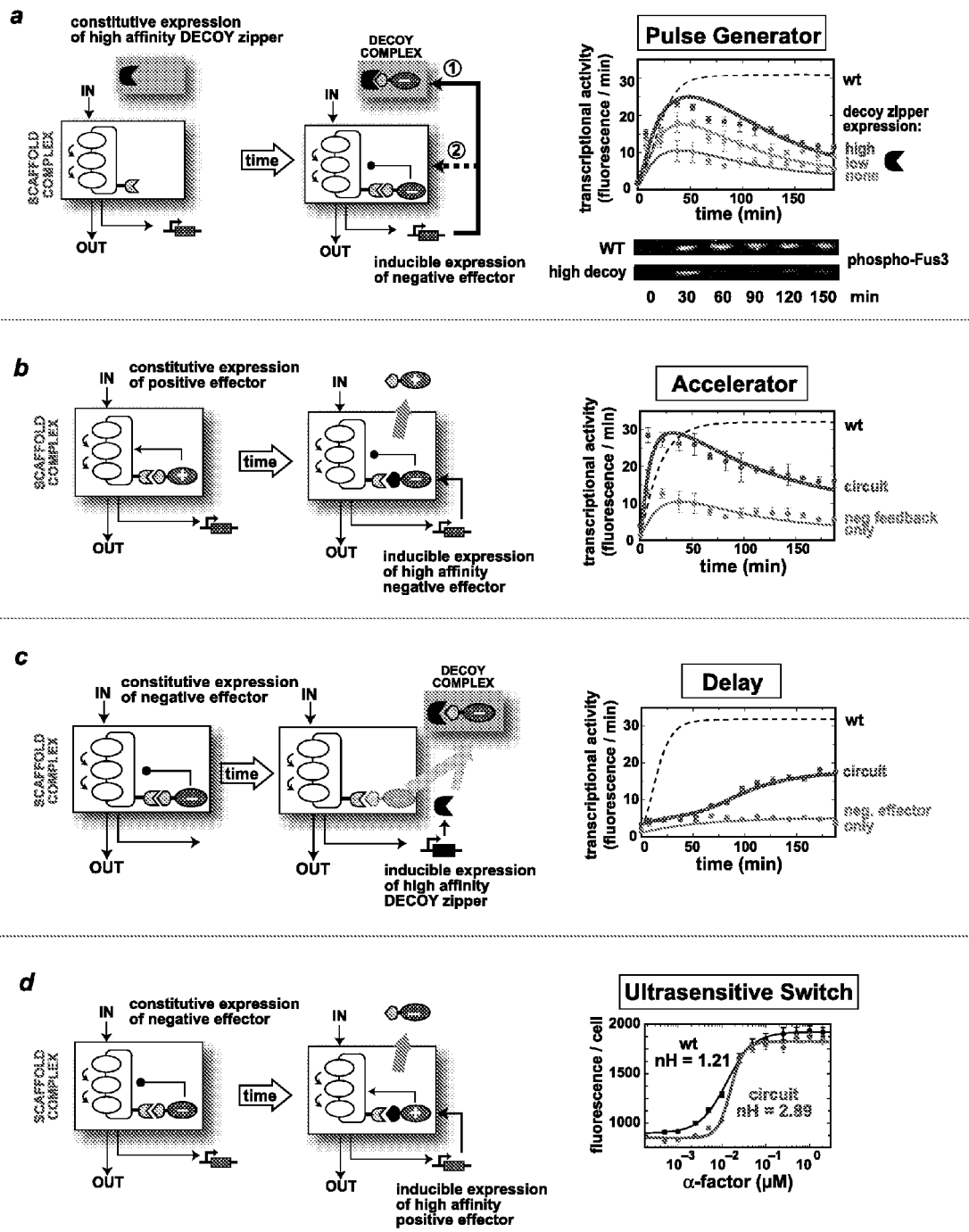
FIG. 4. Recruitment-based molecular toolkit: (a) Pulse response behavior generated by taking the simple negative feedback loop and adding a constitutively expressed decoy zipper; (b) Accelerated circuit response time generated by constitutively expressing a recruited positive effector in combination with the simple negative feedback loop; (c) Delayed response circuit generated by constitutively expressing a negative effector and inducibly expressing a decoy zipper; (d) An ultrasensitive switch built by constitutively expressing a negative effector with a weak zipper and combining it with the simple positive feedback loop.

FIG. 4. Recruitment-based molecular toolkit can be used to engineer highly diverse pathway architectures and response behaviors. (a) Pulse response behavior can be generated by taking the simple negative feedback loop (FIG. 2) and adding a constitutively expressed decoy zipper (GST-zipper) that competes with the Ste5 scaffold zipper. The negative effector (Msg5-zipper) is complementary to both the Ste50-zipper and the decoy zipper, but the decoy zipper binds with higher affinity (Kd=6.1 nM vs. 41 nM). Thus when the pathway is induced and the negative effector is expressed, the decoy initially acts as a sink that prevents the effector from binding to the scaffold and exerting any effect on pathway output. Only after the decoy is saturated will the negative effector bind to the scaffold and repress pathway flux. Experimental circuit behavior is shown on the right, monitored by pFus1-GFP transcriptional reporter (top) and anti-phospho-Fus3 western blot (bottom). Increased constitutive expression of the decoy zipper leads to increasingly sharper pulse response (constitutive promoters: low, pSte5; high, pAdh1).

(b) Accelerated circuit response time can be generated by constitutively expressing a recruited positive effector (promoter: pSte5; gene: Ste50-zipper) in combination with the simple negative feedback loop (FIG. 2). Time course of activation (right) shows a faster rise time—the circuit reaches the maximal output observed for the wild-type circuit, but in <20 minutes instead of ~75 minutes.

(c) Delayed response circuit can be generated by constitutively expressing a negative effector (promoter: pSte5; gene: Msg5-zipper) and inducibly expressing a decoy zipper that is complementary to the negative effector-zipper (promoter: pFIG .1; gene: GST-zipper), but which binds with higher affinity than the Ste5-zipper (Kd=6.1 nM vs. 41 nM). The negative effector maintains pathway in a repressed state until sufficient decoy zipper is expressed to relieve this repression. This circuit is essentially an inverted negative feedback loop, e.g. a positive feedback loop.

(d) An extreme ultrasensitive switch can be built by constitutively expressing a negative effector (promoter: pSte5; gene: Msg5-zipper) with a weak zipper and combining it with the simple positive feedback loop of FIG. 2 (inducible expression of a positive effector Ste50 from pFig1 promoter). Here, the positive effector is fused to zipper with higher affinity than the negative effector (Kd=6.1 nM vs. 41 nM), thus the positive effector should effectively displace the negative effector upon expression. This circuit is essentially a double positive loop (induction of positive effector AND displacement of negative effector). Dose-response analysis (right) shows significantly increased ultrasensitivity (apparent Hill coefficient nH ~2.9, compared to the wild-type nH=1.2 and the simple positive feedback loop nH=2.3).

Additional embodiments encompass combinations of the foregoing particular embodiments, and methods of doing business comprising promoting, marketing, selling and/or licensing a subject embodiment.

The foregoing description and examples are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

1. A. S. Burack, A. S. Shaw, Curr. Opin. Cell Biol. 12, 211-6 (2000)
2. T. Pawson, J. D. Scott, Science 19, 2075-80 (1997)
3. R. P. Bhattacharyya, A. Remenyi, B. J. Yeh, W. A. Lim, Annu. Rev. Biochem. 75, 655-80 (2006)
4. B. N, Kholodenko, Nat. Rev. Mol. Cell Biol. 7, 165-76 (2006).
5. J. W. Locasale, A. S. Shaw, A. K. Chakraborty, Proc Natl Acad Sci USA 104: 13307-12 (2007)
6. J. E. Ferrell, Sci STKE 2000: PEI (2000)
7. K. Y. Choi, B. Satterberg, D. M. Lyons, E. A. Elion, Cell 3, 499-512 (1994)
8. J. A. Printen, G. F. Sprague, Genetics 138, 609-19 (1994)
9. S. H. Park, A. Zarrinpar, W. A. Lim, Science 299, 1061-4 (2003)
10. K. Harris, R. E. Lamson, B. Nelson, T. R. Hughes, M. J. Marton, C. J. Roberts, C. Boone, P. M. Pryciak, Curr. Biol. 11, 1815-24 (2001)
11. M. A. Poritz, S. Malmstrom, M. K. Kim, P. J. Rossmeissl, A. Kamb, Yeast 18, 1331-8 (2001).
12. A. Colman-Lerner, A. Gordon, E. Serra, T. Chin, O. Resnekov, D. Endy, C. G. Pesce, R. Brent, Nature 437, 631-2 (2005)
13. S. Paliwal, P. A. Iglesias, K. Campbell, Z. Hilioti, A. Groisman, A. Levchenko, Nature 446, 46-51 (2007)
14. J. E. Ferrell, E. M. Machleder, Science 280, 895-8 (1998)
15. C. J. Marshall, Cell 80, 179-85 (1995)
16. S. Sasagawa, Y. Ozaki, K. Fujita, S. Kuroda, Nat. Cell Biol. 7, 365-73 (2005)
17. L. O. Murphy, J. Blenis, Trends Biochem. Sci. 31, 268-75 (2006)
18. M. Villedieu, E. Deslandes, M. Duval, J. F. Heron, P. Gauduchon, L. Poulain, Gynecol. Oncol. 101, 507-19 (2006)
19. B. K. Choi, C. H. Choi, H. L. Oh, Y. K. Kim, Neurotoxicity 25, 915-24 (2004)
20. S. D. Santos, P. J. Verveer, P. 1. Bastiaens, Nat. Cell Biol. 9, 247-9 (2007)
21. A. Acharya, S. B. Ruvinov, J. Gal, C. Vinson, Biochemistry 41, 14122-31 (2002)
22. M. Ramezani-Rad, Curr. Genet. 43, 161-70 (2003)
23. C. Wu, E. Leberer, D. Y. Thomas, M. Whiteway, Mol. Biol. Cell. 10, 2425-40 (1999)
24. X. L. Zhan, R. J. Deschenes, K. L. Guan, Genes Dev. 11, 1690-702 (1997)
25. J. Andersson, D. M. Simpson, M. Qi, Y. Wang, E. A. Elion, EMBO J. 23, 256476 (2004)
26. R. P. Bhattacharyya, A. Remenyi, Good, M. C., C. J. Bashor, A. M. Falick, W. A. Lim. Science 311, 822-6 (2006)
27. Ignolia, N. T., Murray, A. W., Curr. Biol. 17, 668-77 (2007)
28. N. Barkai, S. Leibler, Nature 387, 913-7 (1997)
29. B. Alberts, A. O. Johnson, J. Lewis, M. Raff, D. Bray, K. Hopkin, P. Walter, Essential Cell Biology. (Garland Science/Taylor & Francis Group, ed. 2, 2003)
30. N. Rosenfeld, M. B. Elowtiz, U. Alon, J. Mol. Biol. 323: 785-93 (2002)
31. M. Ptashne, A. Gann, Genes and Signals. (Cold Spring Harbor Laboratory Press, 1st ed., 2001)
32. D. C. Popescu, A. J. Ham, B. H. Shieh, J. Neurosci. 26, 8570-7 (2006)

33. K. Scott, C. S. Zuker, Nature 395, 805-8 (1998)
34. F. D. Smith, L. K. Langeberg, J. D. Scott, Trends Biochem. Sci. 31, 316-23 (2006)
35. S. C. Strickfaden, M. J. Winters, G. Ben-Ari, R. E. Lamson, M. Tyers, P. M. Pryciak, Cell 128:519-31 (2007).

What is claimed is:

1. A yeast cell comprising a synthetic, feedback-regulated MAP kinase pathway having a signaling input and output, comprising:
    (a) a MAP kinase signaling pathway complex fused to a first binding partner; and
    (b) a MAP kinase signaling pathway effector fused to a second binding partner, wherein:
        (i) the first and second binding partners bind to recruit the effector to the complex;
        (ii) the effector functionally modulates the complex to provide a modulated output; and
        (iii) the modulated output in turn modulates effector activity, providing a regulatory feedback loop to the pathway.

2. The yeast cell of claim 1, wherein the effector is a positive effector providing an increased, modulated output.

3. The yeast cell of claim 1, wherein the effector is a negative effector providing a decreased, modulated output.

4. The yeast cell of claim 1, wherein the modulated output increases effector activity to create a positive feedback loop.

5. The yeast cell of claim 1, wherein the modulated output decreases effector activity to create a negative feedback loop.

6. The yeast cell of claim 1, wherein the effector is a negative effector providing a decreased modulated output, and the yeast cell constitutively expresses a decoy that competes with the complex for the negative effector, effectively creating a pulse generator signaling pathway.

7. The yeast cell of claim 1, wherein the effector is a positive effector providing an increased, modulated output, and the yeast cell constitutively expresses the positive effector, and inducibly expresses a negative effector, effectively creating an accelerator signaling pathway.

8. The yeast cell of claim 1, wherein the effector is a negative effector providing a decreased modulated output, and the yeast cell constitutively expresses the negative effector, and inducibly expresses a high-affinity decoy that competes with the complex for the negative effector, effectively creating an delay signaling pathway.

9. The yeast cell of claim 1, wherein the effector is a negative effector providing a decreased modulated output, and the yeast cell constitutively expresses the negative effector, and inducibly expresses a positive effector, that competes with the complex for the negative effector, effectively creating an ultrasensitive switch signaling pathway.

10. A method of making by genetically-engineering a yeast cell of claim 1, comprising genetically-engineering the cell to express the synthetic, feedback-regulated MAP kinase pathway.

11. The yeast cell of claim 1, wherein effector expression is under the control of an output-dependent promoter such that the effector is only expressed after pathway activation.

12. A yeast cell comprising a synthetic, feedback-regulated MAP kinase signaling pathway, comprising:
    a first recombinant gene encoding a first fusion protein comprising a MAP kinase pathway modulator fused to a first binding partner of a pair of recruitment binding partners;
    a second recombinant gene encoding a second fusion protein comprising a scaffold protein of the MAP kinase pathway fused to a second binding partner of the pair of recruitment binding partners;
    wherein the first fusion protein is recruited to the scaffold by the second fusion protein,
    wherein the modulator modulates activity of the MAP kinase pathway which in turn modulates activity of the modulator.

13. The yeast cell of claim 12, wherein the modulator is a positive modulator providing an increased, modulated output of the MAP kinase pathway.

14. The yeast cell of claim 12, wherein the modulator is a negative modulator providing a decreased, modulated output of the MAP kinase pathway.

15. The yeast cell of claim 12, wherein expression of the first recombinant gene is under the control of a promoter regulated by an output of the MAP kinase pathway, wherein the modulated output increases modulator expression to create a positive feedback loop.

16. The yeast cell of claim 12, wherein expression of the first recombinant gene is under the control of a promoter regulated by an output of the MAP kinase pathway, wherein the modulated output decreases modulator expresssion to create a negative feedback loop.

17. The yeast cell of claim 12, wherein the modulator is a negative modulator providing a decreased modulated output, and the yeast cell constitutively expresses a decoy that competes with the complex for the negative modulator, effectively creating a pulse generator signaling pathway.

18. The yeast cell of claim 12, wherein the modulator is a positive modulator providing an increased modulated output, and the yeast cell constitutively expresses the positive modulator, and inducibly expresses a negative modulator, effectively creating an accelerator signaling pathway.

19. The yeast cell of claim 12, wherein the modulator is a negative modulator providing a decreased modulated output, and the yeast cell constitutively expresses the negative modulator, and inducibly expresses a high-affinity decoy that competes with the complex for the negative modulator, effectively creating an delay signaling pathway.

20. The yeast cell of claim 12, wherein the modulator is a negative modulator providing a decreased modulated output, and the yeast cell constitutively expresses the negative modulator, and inducibly expresses a positive modulator, that competes with the complex for the negative modulator, effectively creating an ultrasensitive switch signaling pathway.

* * * * *

UNITED STATES PATENT AND TRADEMARK OFFICE
CERTIFICATE OF CORRECTION

PATENT NO. : 7,879,590 B2
APPLICATION NO. : 12/047767
DATED : February 1, 2011
INVENTOR(S) : Wendell A. Lim and Caleb J. Bashor Page 1 of 1

It is certified that error appears in the above-identified patent and that said Letters Patent is hereby corrected as shown below:

The government support paragraph at col. 1, lines 6-8 should read as follows:

This invention was made with government support under Grant No. N66001-04-1-8901 awarded by the Department of Defense (DARPA) and Grant No. R01 GM055040 awarded by the National Institutes of Health. The government has certain rights in the invention.

Signed and Sealed this
Fifth Day of July, 2011

David J. Kappos
*Director of the United States Patent and Trademark Office*